(12) United States Patent
Steinmetz et al.

(10) Patent No.: US 9,539,412 B2
(45) Date of Patent: Jan. 10, 2017

(54) CATHETER HUB

(71) Applicant: BIO2 MEDICAL, INC., San Antonio, TX (US)

(72) Inventors: Jeffrey N. Steinmetz, Arvada, CO (US); Joseph H. Taber, San Antonio, TX (US)

(73) Assignee: BIO2 MEDICAL, INC., San Antonio, TX (US)

( * ) Notice: Subject to any disclaimer, the term of this patent is extended or adjusted under 35 U.S.C. 154(b) by 63 days.

(21) Appl. No.: 14/504,879

(22) Filed: Oct. 2, 2014

(65) Prior Publication Data

US 2015/0088074 A1 Mar. 26, 2015

Related U.S. Application Data

(62) Division of application No. 13/083,053, filed on Apr. 8, 2011, now Pat. No. 8,870,849.

(60) Provisional application No. 61/322,242, filed on Apr. 8, 2010.

(51) Int. Cl.
*A61M 25/01* (2006.01)
*A61M 25/00* (2006.01)

(52) U.S. Cl.
CPC ......... *A61M 25/01* (2013.01); *A61M 25/0097* (2013.01); *A61M 2025/0006* (2013.01); *A61M 2025/0175* (2013.01); *A61M 2205/586* (2013.01)

(58) Field of Classification Search
CPC .............. A61M 25/01; A61M 25/0113; A61M 25/0097; A61M 2025/0006; A61M 2025/0175
See application file for complete search history.

(56) References Cited

U.S. PATENT DOCUMENTS

| | | | |
|---|---|---|---|
| 4,884,573 A | * | 12/1989 | Wijay ..................... A61L 29/06 604/913 |
| 5,300,086 A | | 4/1994 | Gory et al. .................. 606/200 |
| 5,405,380 A | | 4/1995 | Gianotti et al. .................. 623/1 |
| 5,485,846 A | * | 1/1996 | Webler ..................... A61B 8/12 600/463 |
| 5,533,988 A | | 7/1996 | Dickerson et al. .............. 604/282 |
| 5,549,626 A | | 8/1996 | Miller et al. ................. 606/200 |
| 5,607,466 A | | 3/1997 | Imbert et al. ..................... 623/1 |
| 5,626,602 A | | 5/1997 | Gianotti et al. ............... 606/198 |
| 5,688,249 A | | 11/1997 | Chang et al. ................. 604/198 |
| 5,725,571 A | | 3/1998 | Imbert et al. ..................... 623/1 |

(Continued)

FOREIGN PATENT DOCUMENTS

EP 2 305 339 4/2011 ............ A61M 25/06

OTHER PUBLICATIONS

PCT International Search Report issued in corresponding foreign application, pp. 1-6 (Dec. 26, 2011).

(Continued)

*Primary Examiner* — Andrew Gilbert
(74) *Attorney, Agent, or Firm* — David G. Rosenbaum; Benjamin D. Rotman; Rosenbaum IP, P.C.

(57) ABSTRACT

A catheter hub includes a distal assembly including a distal hub member adapted to be fixedly attached to an outer catheter and a proximal assembly including a proximal hub member adapted to be fixedly attached to an inner catheter disposed through the outer catheter. An elongate member connects the proximal and distal assemblies such that the proximal and distal assemblies can translate longitudinally relative to one another.

16 Claims, 11 Drawing Sheets

(56) References Cited

U.S. PATENT DOCUMENTS

| | | | |
|---|---|---|---|
| 5,733,267 A | 3/1998 | Del Toro | 604/280 |
| 5,772,636 A | 6/1998 | Brimhall et al. | 604/198 |
| 5,827,313 A | 10/1998 | Ream | 606/171 |
| 5,830,188 A | 11/1998 | Abouleish | 604/158 |
| 6,146,415 A | 11/2000 | Fitz | 623/1.11 |
| 6,190,360 B1 | 2/2001 | Iancea et al. | 604/164.09 |
| 6,319,227 B1 | 11/2001 | Mansouri-Ruiz | 604/95.01 |
| 6,695,862 B2 | 2/2004 | Cox et al. | 606/191 |
| 6,709,454 B1 | 3/2004 | Cox et al. | 623/1.16 |
| 6,827,710 B1* | 12/2004 | Mooney | A61B 17/3417 604/167.06 |
| 6,860,898 B2 | 3/2005 | Stack et al. | 623/1.11 |
| 6,939,370 B2 | 9/2005 | Hartley et al. | 623/1.11 |
| 7,105,016 B2 | 9/2006 | Shiu et al. | 623/1.12 |
| 7,235,061 B2 | 6/2007 | Tsugita | 604/104 |
| 7,261,708 B2 | 8/2007 | Raulerson | 604/523 |
| 7,276,044 B2 | 10/2007 | Ferry et al. | 604/95.01 |
| 7,297,142 B2* | 11/2007 | Brock | A61B 90/36 348/65 |
| 7,300,430 B2 | 11/2007 | Wilson et al. | 604/523 |
| 7,371,210 B2 | 5/2008 | Brock et al. | 600/114 |
| 7,476,244 B2 | 1/2009 | Buzzard et al. | 623/1.11 |
| 7,479,150 B2* | 1/2009 | Rethy | A61B 17/3403 600/184 |
| 7,556,635 B2 | 7/2009 | Mazzocchi et al. | 606/200 |
| 7,621,946 B2 | 11/2009 | Turner et al. | 623/1.11 |
| 7,635,382 B2 | 12/2009 | Pryor | 623/1.11 |
| 7,648,525 B2 | 1/2010 | Yanuma et al. | 623/1.11 |
| 7,658,757 B2 | 2/2010 | Moberg et al. | 623/1.11 |
| 7,674,282 B2 | 3/2010 | Wu et al. | 623/1.11 |
| 7,691,139 B2 | 4/2010 | Baker et al. | 623/1.11 |
| 7,727,185 B2 | 6/2010 | Weitzner et al. | 604/95.01 |
| 7,766,856 B2 | 8/2010 | Ferry et al. | 604/19 |
| 7,766,894 B2 | 8/2010 | Weitzner et al. | 604/509 |
| 8,104,479 B2 | 1/2012 | Glynn et al. | 128/853 |
| 8,172,083 B2* | 5/2012 | Mahalingam | B65D 25/04 206/429 |
| 8,297,181 B2* | 10/2012 | Yang | A47J 37/1209 219/438 |
| 8,298,181 B2* | 10/2012 | Perez | A61M 5/3287 604/115 |
| 8,343,096 B2 | 1/2013 | Kirschenman et al. | 604/95.04 |
| 8,414,473 B2* | 4/2013 | Jenkins | A61B 1/0014 600/104 |
| 8,459,266 B2 | 6/2013 | Glynn et al. | 128/853 |
| 8,870,849 B2* | 10/2014 | Steinmetz | A61M 25/0097 604/528 |
| 2002/0165497 A1 | 11/2002 | Greene | 604/198 |
| 2003/0014039 A1* | 1/2003 | Barzell | A61B 8/4209 606/1 |
| 2003/0216771 A1 | 11/2003 | Osypka et al. | 606/191 |
| 2005/0070878 A1 | 3/2005 | Triplett et al. | 604/523 |
| 2006/0235436 A1* | 10/2006 | Anderson | 606/130 |
| 2007/0021648 A1* | 1/2007 | Lenker | A61M 25/0097 600/29 |
| 2007/0060879 A1 | 3/2007 | Weitzner et al. | 604/95.04 |
| 2007/0173786 A1 | 7/2007 | Recinella et al. | 604/523 |
| 2007/0233044 A1 | 10/2007 | Wallace et al. | 604/528 |
| 2007/0260221 A1 | 11/2007 | Chesin | 604/523 |
| 2008/0045892 A1 | 2/2008 | Ferry et al. | 604/95.01 |
| 2009/0062840 A1 | 3/2009 | Angel | 606/200 |
| 2009/0131872 A1 | 5/2009 | Popov | 604/164.01 |
| 2010/0004730 A1* | 1/2010 | Benjamin | A61F 2/95 623/1.11 |

OTHER PUBLICATIONS

Examination Report issued in corresponding foreign application, European Patent Application No. 117766811.1, pp. 1-7 (Aug. 13, 2013).

Official Action issued in corresponding foreign application, AU 2011237339, pp. 1-7 (May 23, 2014).

* cited by examiner

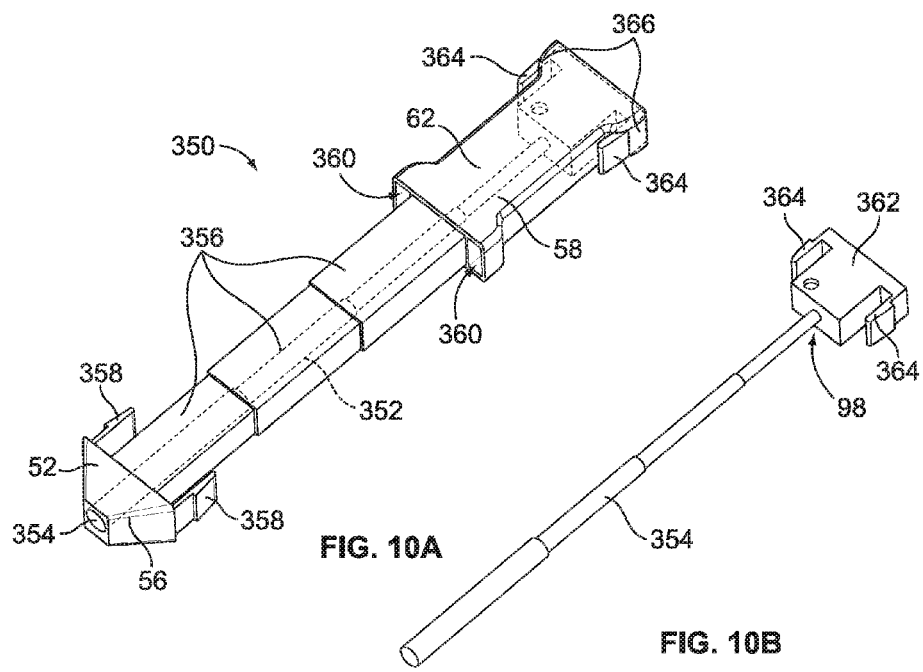
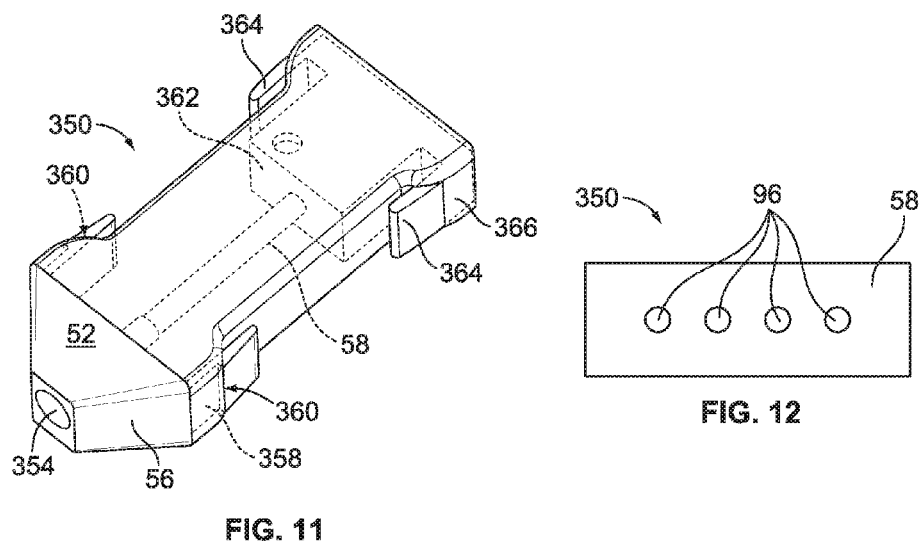

CATHETER HUB

CROSS-REFERENCE TO RELATED APPLICATIONS

The present application claims priority from and is a divisional from U.S. patent application Ser. No. 13/083,053, filed Apr. 8, 2011, which issued as U.S. Pat. No. 8,870,849 on Oct. 28, 2014, which claims priority from U.S. Provisional Patent Application Ser. No. 61/322,242, filed on Apr. 8, 2010, all herein incorporated by reference in their entireties.

FIELD OF THE INVENTION

The present invention relates generally to catheters and more particularly to catheter hub assemblies.

BACKGROUND OF THE INVENTION

An intravascular medical device may be attached to a distal end of an inner catheter and held within an outer catheter for introduction into a patient. The intravascular medical device may, for example, be a vascular or vena cava filter for capturing embolic material in the blood flow, a stent, an embolic filter, an angioplasty balloon, a drug delivery device, or similar such minimally invasive intravascular device.

The inner and outer catheters may be introduced into a patient over a guidewire. Upon positioning the intravascular medical device within the vasculature at the site of treatment, the outer catheter is retracted from the inner catheter to release the device from the outer catheter. Because the inner and outer catheters are typically made from a longitudinally flexible material to allow navigation of the catheter assembly through the vasculature during insertion to the site of treatment, neither of the inner or outer catheters may have good resistance to kinking. The kinking resistance may not be an issue during catheter insertion because the inner and outer catheters are concentrically disposed and may be disposed over a guide wire. However, upon reaching the site of treatment, kinking of the inner catheter during refraction of the outer catheter may present problems to a medical professional during a procedure An intravenous catheter introducer is known in the art and includes a pair of telescoping members disposed between a hub on a distal end and a flash housing on a proximal end of the telescoping members. Prior to catheter introduction, the telescoping members are retracted such that the hub and flash housing are juxtaposed and a sharpened cannula tip extends from a distal end of the catheter introducer. The cannula tip is used to pierce a blood vessel such that the peripheral intravenous catheter can be introduced into the blood vessel over the cannula. The catheter introducer is subsequently withdrawn exposing the sharpened cannula tip now soiled with blood from the patient. The sharpened cannula tip is subsequently covered by a portion of the catheter introducer by pulling the hub and the housing apart until the telescoping members lock out further movement.

Kinking of the cannula is not an issue in catheter introducers because friction of the hub and housing being pulled apart provides a tension force to the cannula. In contrast, kinking can be a problem for a catheter hub having inner and outer catheter members because the action of withdrawing the outer catheter over the inner catheter frictionally provides a longitudinally compressive force to the inner catheter. Accordingly, there remains a need for an improved catheter hub that addresses the kinking problem.

SUMMARY OF THE INVENTION

In one aspect of the present invention, a catheter hub includes a distal assembly including a distal hub member adapted to be fixedly attached to an outer catheter and a proximal assembly including a proximal hub member adapted to be fixedly attached to an inner catheter disposed through the outer catheter. An elongate member connects the proximal and distal assemblies such that the proximal and distal assemblies are capable of longitudinal translation relative to one another.

In another aspect of the invention, a catheter hub includes a distal hub member adapted to be fixedly attached to an outer catheter, a proximal hub member adapted to be fixedly attached to an inner catheter disposed through the outer catheter, a proximal member, and a distal member. An elongate member connects the proximal and distal members. At least one of the proximal and distal members is slidably attached to the elongate member. The distal member is attached to the distal hub member and the proximal member is attached to the proximal hub member.

In a further aspect of the invention, a catheter hub includes a distal hub member adapted to be fixedly attached to an outer catheter and a proximal hub member adapted to be fixedly attached to an inner catheter disposed through the outer catheter. A telescoping member connects the proximal and distal hub members. The proximal hub member connects to the distal hub member when the telescoping member is in a longitudinally collapsed state.

The foregoing summary, as well as the following detailed description of the preferred embodiments, will be understood when read in conjunction with the appended drawings.

BRIEF DESCRIPTION OF THE FIGURES

FIG. 10A is an isometric view of yet another embodiment of a hub assembly in an extended state; and FIG. 10B is an isometric view of the collapsible tube within the telescoping member.

FIG. 11 is an isometric view of the hub assembly of FIG. 10 in a collapsed state.

FIG. 12 is proximal elevation of the hub assembly of FIG. 10.

The foregoing and other features and advantages of the invention are apparent from the following detailed description of exemplary embodiments, read in conjunction with the accompanying drawings, wherein like structural or functional elements are designated by like reference numerals.

DETAILED DESCRIPTION OF THE PREFERRED EMBODIMENTS

Figure 1:
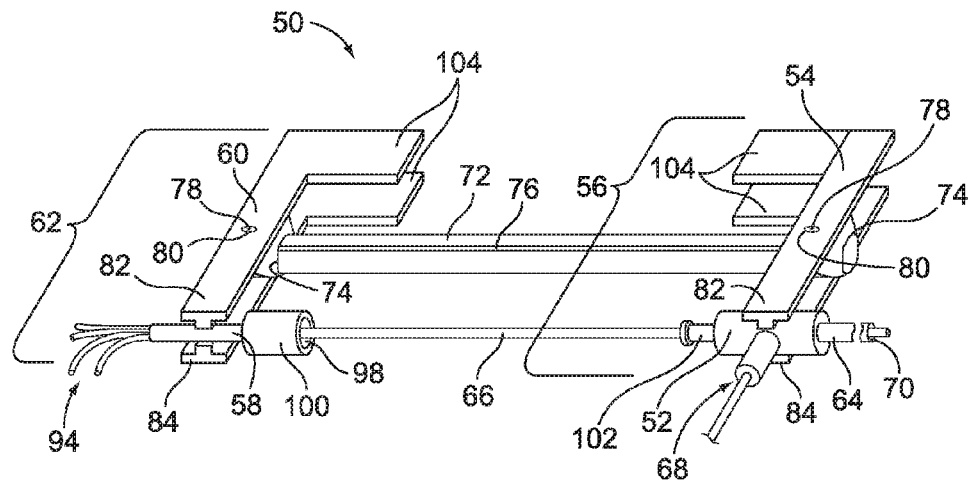
FIG. 1 is an isometric view of an embodiment of a hub assembly in an extended state.

In the following description, spatial orientation descriptors "distal" and "proximal" are used relative to the longitudinal axis of the catheter assembly. Thus, a "proximal" side refers to a side of an element generally facing the medical professional and away from the patient and, conversely, a "distal" side refers to a side of an element generally facing away from the medical professional and toward the patient. Likewise a pair of elements described as "proximal" and "distal" elements are understood to have the same spatial relationship as described hereinabove for the sides of an element.

Generally speaking, the catheter hub assembly includes an outer catheter and an inner catheter in which the inner catheter is concentrically and coaxially positioned within the outer catheter and the outer catheter and inner catheter are axially moveable relative to one another. More particularly, a proximal catheter hub limits and/or controls the relative axial movement of the inner catheter relative to the outer catheter and that provides a locked position and kinking resistance for the inner catheter during its axial movement relative to the outer catheter. In some embodiments, proximal and/or distal hub components are small relative to the larger translation distance between the proximal and distal hub components.

Referring to FIGS. 1-4, in one embodiment, a hub assembly 50 for a catheter is illustrated in an expanded state. In one embodiment, the catheter is a central access catheter, although, the hub assemblies may be applied to other delivery systems. The hub assembly 50 generally comprises a distal assembly 56 longitudinally engaged with a proximal assembly 62 by at least one elongate member 72. The distal assembly 56 includes a distal hub member 52 and a distal member 54, whereby the distal hub member 52 may be removably attached to the distal member 54. Likewise, the proximal assembly 62 includes a proximal hub member 58 and a proximal member 60, whereby the proximal hub member 58 may be removably attached to the proximal member 60. Each of the proximal and distal members 60, 54 may include first and second members 82, 84 for removable attachment to the proximal and distal hub members 58, 52. The proximal hub member 58 and the distal hub member 52 are operably coupled by an inner catheter 66.

The distal hub member 52 is adapted to be distally attached to an outer catheter 64 of a central access catheter. The attachment of the distal hub member 52 to the outer catheter 64 may be a fixed attachment, a removable attachment, a rotatable attachment, a magnetic attachment, or a slidable attachment, and may be via a fastener, an adhesive, a press fit, a snap fit, or via any method of attachment. Similarly, the proximal hub member 58 is adapted to be attached to the inner catheter 66 that is slidably disposed through the outer catheter 64. The attachment of the proximal hub member 58 to the inner catheter 66 may be a fixed attachment, a removable attachment, a rotatable attachment, a magnetic attachment, or a slidable attachment, and may be via a fastener, an adhesive, a press fit, a snap fit, male and female luers, or via any method of attachment. The distal hub member 52 and/or the proximal hub member 58 may also include a port 68 (illustrated on the distal hub member 52 in FIGS. 1-4) that allows fluid to be introduced through an interior space 70 between the inner and outer catheters 66, 64 when the distal hub member 52 is engaged with the proximal hub member 58. Alternatively, the port 68 may include multiple ports, as to couple with multiple lumens in the outer catheter 66 or converge into a single lumen in the outer catheter 66. In one embodiment, the interior space 70 is concentrically disposed between the inner catheter 66 and the outer catheter 64.

Figure 2:
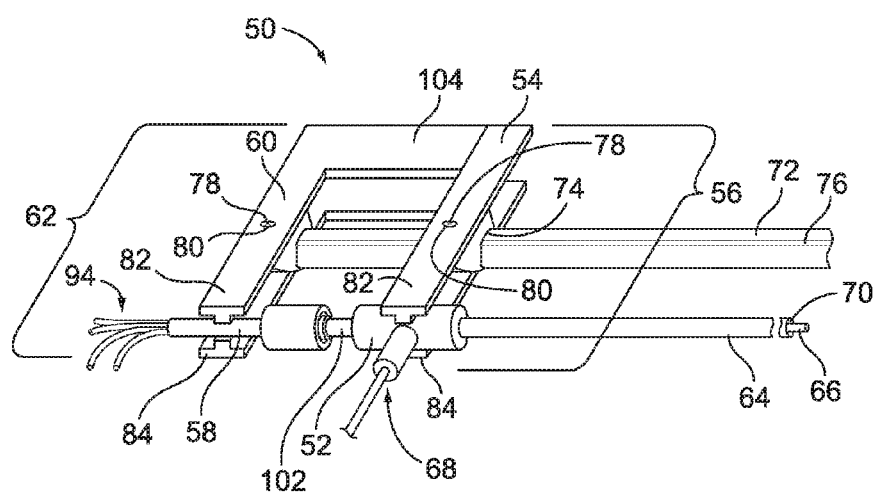
FIG. 2 is an isometric view of the hub assembly of FIG. 1 in a collapsed state.

The at least one elongate member 72 connects the proximal assembly 62 and the distal assembly 56, such that the proximal and distal assemblies 62, 56 may be translated longitudinally relative to one another, as shown in the contracted state in FIG. 2. In one embodiment, the at least one elongate member 72 resides laterally adjacent to and parallel with the inner catheter 66. In this embodiment, the proximal member 60 is part of the proximal assembly 62 and the distal member 54 is part of the distal assembly 56, such that the elongate member 72 connects the proximal member 60 and the distal member 54 in a manner that permits their relative movement. For example, the proximal member 60 may be slidably attached to the elongate member 72 through and the distal member 54 may be fixedly attached to the elongate member 72 through. Alternatively, for example, the distal member 54 may be slidably attached to the elongate member 72 and the proximal member 60 may be fixedly attached to the elongate member 72, or both the proximal member 60 and the distal member 54 may be slidably attached to the elongate member 72.

As shown in FIGS. 1-2, the proximal and distal assemblies 62, 56 (or the proximal and distal members 60, 54) are translated relatively toward one another, and the inner catheter 66 slidably translates distally through the outer catheter 64. The proximal hub member 58 includes a first connector 100 disposed on the distal side of the proximal hub member 58 and positioned coaxially over the inner catheter 66. The distal hub member 52 includes a second connector 102 on the proximal side of the distal hub member 52 and positioned coaxially over the inner catheter 66. When the proximal and distal assemblies 62, 56 (or the proximal and distal members 60, 54) are brought together, as illustrated in FIG. 2, the first and second connectors 100, 102 engage with one another. For example, the first connector 100 may include a lumen concentrically larger than the exterior surface of the second connector 102, whereby the second connector 102 concentrically or coaxially fits within the first connector 100. Alternatively, the second connector 102 may include a lumen concentrically larger than the exterior surface of the first connector 100, whereby the first connector 100 concentrically or coaxially fits within the second connector 102. The connection of the first and second connectors 100, 102 may be by fastener, an adhesive, a press fit, a snap fit, or via any method of connection for the proximal hub member 58 and the distal hub member 52 to be connected.

Figure 3:
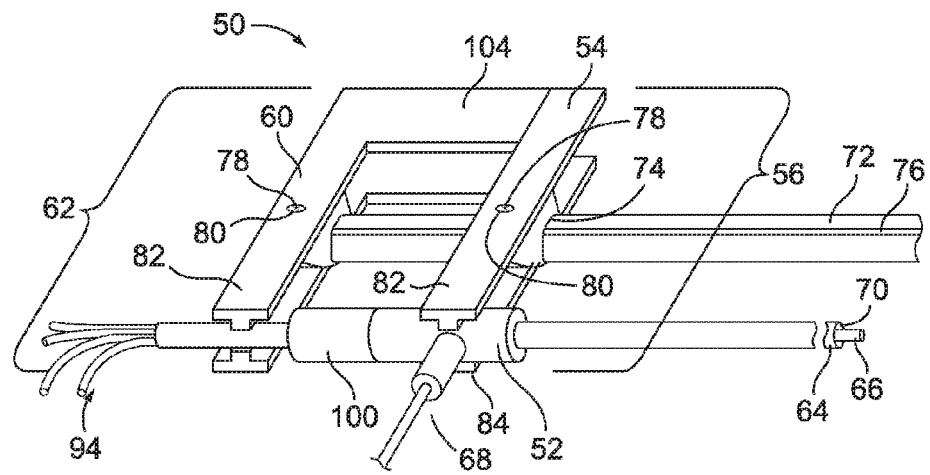
FIG. 3 is an isometric view of the hub assembly of FIG. 1 in a connected state.

As shown in FIGS. 1-3, the slidable attachment of the proximal member 60 or the distal member 54 to the elongate member 72 may be via an aperture 74 disposed through the proximal member 60 and/or the distal member 54. The aperture 74 is adapted to accommodate the elongate member 72 and is further adapted to allow the proximal member and/or the distal member 60, 54 to slide longitudinally thereon. In one embodiment, the aperture 74 coaxially accommodates the elongate member 72. Alternatively, the aperture 74 may accommodate any configuration of the elongate member 72, including, but not limited to a polygonal configuration, a square configuration, an elliptical configuration, hexagonal configuration, and the like. In one embodiment, a slidable connection between the elongate member 72 and one or both of the proximal member 60 and the distal member 54 may be facilitated via a T-shaped tongue and groove (not shown), a C-clamp partially or entirely surrounding a cross-section of the elongate member (not shown), a C-clamp having inwardly pointing shoulders accommodated by a pair of oppositely disposed longitudinal grooves on the elongate member 72 (not shown), or by any method of slidable attachment as known in the art. Either of both of the elongate member 72 or aperture 74 may be provided with at least one restriction element (not shown) that intermittently interrupts the longitudinal movement of the proximal member 60 and/or the distal member 54 along the elongate member 72 through the aperture 74. Examples of restriction elements may include, for example, detents and cooperating projections, interference rings or similar structures.

A fixed attachment of the proximal member 60 or the distal member 54 to the elongate member 72 may be via a fastener, an adhesive, a press fit, a snap fit, or via any method of attachment as known in the art. For example, as illustrated in FIGS. 1-3, in one embodiment, a surface groove 76 is disposed longitudinally along the exterior surface of the elongate member 72. The surface groove 76 accommodates a set screw 78 disposed through an aperture 80 in one or both of the proximal and distal members 60, 54. The aperture 80 may be threaded, such that the set screw 78 may be tightened to fixedly attach the proximal member 60 or the distal member 54 at a desired location on the elongate member 72. Further, the proximal and/or distal member 60, 54 may include a rib (not shown) on the interior surface of the proximal or distal member 60, 54, whereby the rib is adapted to extend into the surface groove 76 to inhibit relative rotation between the proximal and/or distal member 60, 54 and the elongate member 72. Alternatively, the elongate member 72 may include at least two surface grooves 76 disposed longitudinally along the exterior surface, such as to accommodate a set screw 78 on the top and bottom portions of the proximal and distal members 60, 54.

FIG. 3 illustrates the first and second connectors 100, 102 (and therefore the proximal and distal hub members 58, 52) in a connected state, such that in this embodiment, the connector 102 is within the connector 100 and is therefore not visible. The first and second connectors 100, 102 may be connected to one another via a quick-connect fitting, a press fit, a snap fit, a threaded connection, or by any method of detachable attachment as known in the art. Subsequent to attachment of the proximal and distal hub members 58, 52, translating of the outer catheter 64 proximally relative to the inner catheter 66 may proceed. The proximal and distal members 60, 54 may remain attached to the proximal and distal hub members 58, 52, as illustrated by FIG. 3. Alternatively, in this embodiment, the proximal and distal members 60, 54 may be detached from the proximal and distal hub members 58, 52, as disclosed hereinabove.

Each of the proximal and distal members 60, 54 may include longitudinal extensions 104, as illustrated in FIGS. 1-4, which give the proximal and distal members 60, 54 a substantially L-shape. Alternatively, the proximal and distal member 60, 54 may have a substantially H-shape or winged shaped, such as to accommodate the longitudinal extensions 104. The longitudinal extensions 104 may facilitate a larger surface on which to apply the above-noted force to counter the closing force of the torsional springs. The extensions 104 may also mesh together or operably engage, as illustrated in FIGS. 2-4A, when the hub assembly 50 is in a collapsed state. Such meshing or engagement facilitates ease of handling and may alert a medical professional that the first and second connectors 100, 102 are in contact and ready to be connected or that the connectors 100 and 102 have been engaged and the assemblies 56, 62 can be removed.

Figure 4A:
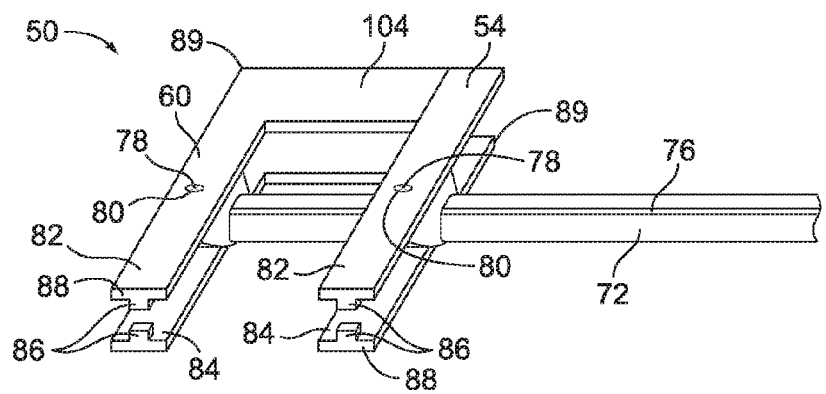
FIG. 4A is an isometric view of the hub assembly without the proximal hub or the distal hub members.
Figure 4B:
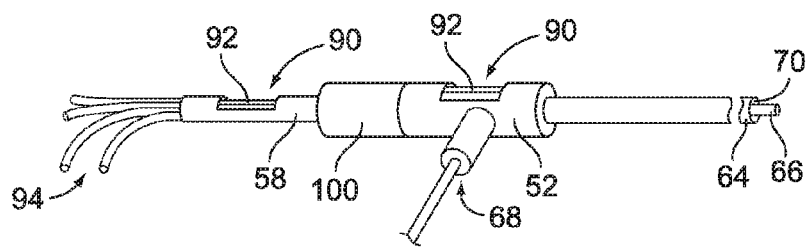
FIG. 4B is an isometric view of the hub assembly of FIG. 1 in a detached state without the proximal and distal members.

In one embodiment, as illustrated in FIGS. 4A-4B, the distal hub member 52 is detachable from the distal assembly 56 and the proximal hub member 58 is detachable from the proximal assembly 62. Further, the distal hub member 52 is detachably attached to the distal member 54 and the proximal hub member 58 is detachably attached to the proximal member 60. A detachable attachment of the distal hub member 52 to the distal member 54 and/or of the proximal hub member 58 to the proximal member 60 may be via a fastener, a quick-connect fitting, an adhesive, a press fit, a clamp, a snap fit, a threaded connection, or by any method of detachable attachment as known in the art.

For example, still referring to FIG. 4A, in this embodiment, each of the first and second members 82, 84 of the proximal and distal members 60, 54 include a raised or slotted tooth or teeth 86 proximate to a first end 88 of the first and second members 82, 84. Each of the first and second members 82, 84 may be configured to pivot around the aperture 74 and to include a spring (not shown) on the second end 89, for example, a torsion spring, to force the first and second members 82, 84 towards each other and in a closed position at the first end 88. Each of the proximal and distal hub members 58, 52 includes a notch 90 disposed transversely thereacross. The notch 90 may include a longitudinal rib 92 disposed therein. When each of the proximal and distal members 60, 54 is closed by the force of the torsional spring, the tooth or teeth 86 is adapted to accommodate the longitudinal rib 92 in the transverse notch 90. The proximal and distal members 60, 54 are thereby detachably attached to the proximal and distal hub members 58, 52, respectively. The proximal and distal members 60, 54 may be detached from the proximal and distal hub members 58, 52, respectively, by applying a force to counter the closing force of the torsional springs.

As shown in FIGS. 1-3, a plurality of tubes 94 enter the proximal hub member 58 via a plurality of first hub apertures 96 (see FIG. 12) that are sized to accommodate the plurality of tubes 94. Each of the plurality of tubes 94 includes one or more lumens that are brought together in the inner catheter 66, which exits the proximal hub member 58 via a second hub aperture 98 (see FIG. 1). The plurality of tubes 94 and/or lumens therein may be segregated or combined within the inner catheter 66 as desired or as needed such that the inner catheter 66 may include a single lumen or a plurality of lumens disposed therethrough. Bioactive agents, flushing fluids, pressurized mechanical thrombolytic fluids, or other fluids may be infused through the plurality of tubes 94 via the one or more lumens through the inner catheter 66 to the site of treatment. Further details of an inner catheter including a plurality of lumens may be found in U.S. patent application Ser. No. 11/849,225, filed on Aug. 31, 2007, and incorporated in its entirety herein. The illustration of four tubes 94 in FIGS. 1-4 is exemplary only; the proximal hub member 58 may accommodate any number of tubes as may be desired or needed, for example, between about 1-10 tubes, alternatively, between about 1-5 tubes.

In operation, the hub assembly 50 begins in an extended state, as illustrated in FIG. 1. The inner and outer catheters 66, 64 are positioned within a vascular member such that, for example, a distal end of the outer catheter 64 is proximate to a site of treatment. A distal end of the inner catheter 66 may include an intravascular medical device, for example, a stent, a graft, a filter, imaging device, and the like attached thereto, such that the intravascular medical device is held within the outer catheter 64. The intravascular medical device is deployed from the outer catheter 64 by longitudinally translating the outer catheter 64 proximally relative to the inner catheter 66. While this operation may also be thought of as translating the inner catheter 66 distally relative to the outer catheter 64, and is accomplished by longitudinally translating the proximal and distal assemblies 62, 56 closer together. It is generally preferable to maintain the medical device associated with the inner catheter 66 in a stationary position and withdraw the outer catheter 64 to expose and deploy the medical device. In this embodiment, longitudinally translating the proximal and distal assemblies 62, 56 closer together has the effect of translating the proximal and distal members 60, 54 closer together.

Figure 5:
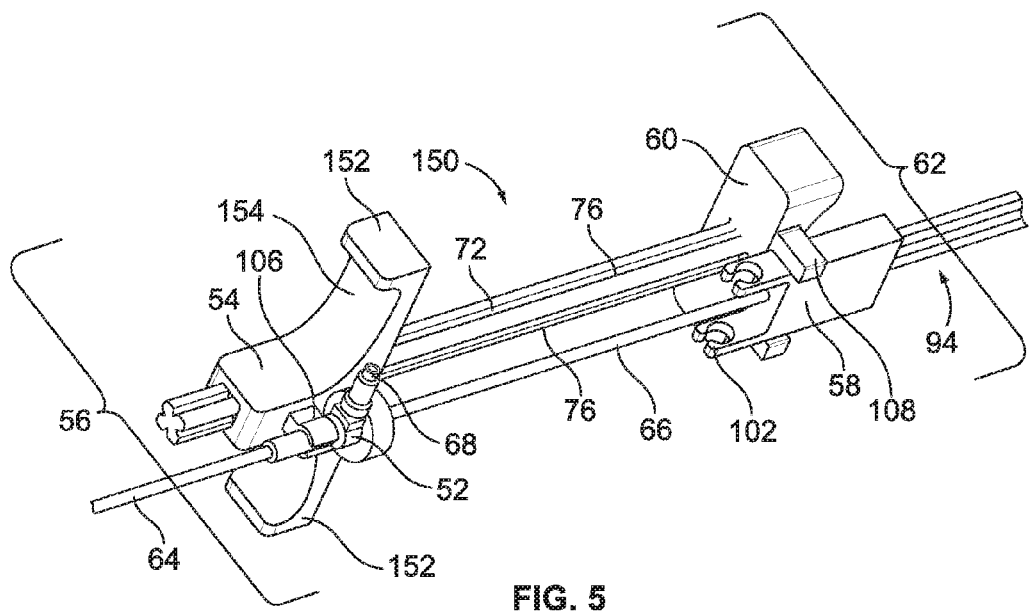
FIG. 5 is an isometric view of another embodiment of a hub assembly in an extended state.

Another embodiment of a hub assembly 150 illustrated in FIGS. 5-6, which is similar to the hub 50 described hereinabove with regard to FIGS. 1-4. However, in this embodiment, for example, the elongate member 72 has a generally square cross-section and includes the surface groove 76 extending longitudinally along each side of the elongate member 72, such that there are four surface grooves 76 on the elongate member 72. Alternatively, the elongate member 72 may include two surface grooves 76 on opposing sides or adjacent sides, three surface grooves 76, and the like. The elongate member 72 may, for example, be attached to the proximal member 60 via a press fit into the aperture 74. Alternatively, the elongate member 72 and the proximal member 60 may, for example, be a single integrally manufactured member. The distal assembly 56 comprises the distal member 54 that connects onto the distal hub member 52 via connector 106, for example, a snap fit. Likewise, the proximal assembly 62 comprises a proximal member 60 that connects onto the proximal hub member 58 via connector 108, for example, a snap fit. As illustrated by FIG. 5, the proximal hub member 58 connects to the distal hub member 52 via, for example, a snap fit with the connectors 102 when the proximal hub member 58 is translated towards distal hub member 52. The port 68 extends from the distal hub member 52 and may additionally extend through the snap-fit connector for stability. Only a single connector 106 is illustrated; however, a second snap-fit connector (not shown) may extend from the distal member 54 from a side thereof opposite the first snap-fit connector 106 or adjacent to the first snap-fit connector 106. Likewise, a mating pair of third snap fit connectors (not shown) may extend from the proximal hub member 58 on a side thereof opposite the proximal member 60 and from the distal hub member 52 on a side thereof opposite the distal member 54.

Figure 6A:
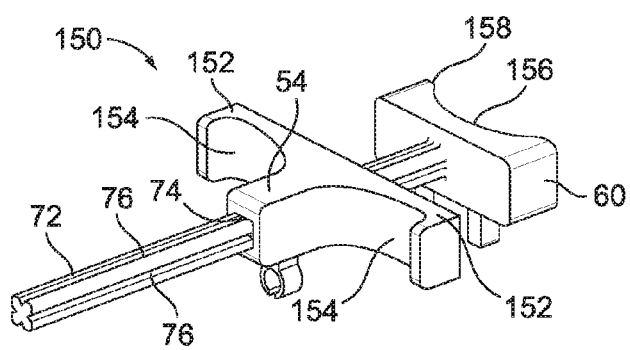
FIG. 6A is an isometric view of the hub assembly of FIG. 5 in a connected state for the proximal and distal members.
Figure 6B:
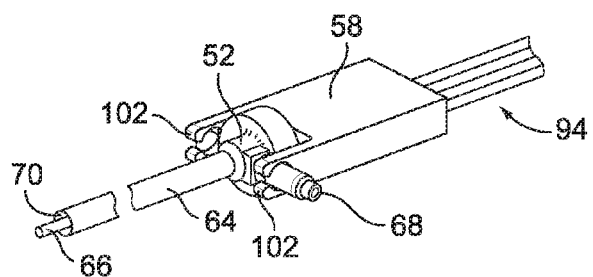
FIG. 6B is an isometric view of the hub assembly of FIG. 5 in a connected state for the proximal and distal hub members.

Referring to FIGS. 5 and 6A, the distal member 54 comprises at least two lateral wings 152 that are adapted to accommodate a finger on a distal side 154 of each of the lateral wings 152. As shown in FIG. 6A, the proximal member 60 comprises a longitudinally centered central depression 156 on a proximal side 158 thereof. The central depression 156 is adapted to accommodate a thumb or other pressing device. Together, the lateral wings 152 and the central depression 156 facilitate translating the proximal and distal assemblies 62, 56 toward one another ergonomically using only three fingers. Alternatively, two fingers may be used or other mechanical devices that may couple to the proximal and distal assemblies 62, 56 for translation towards each other. FIG. 6A illustrates the proximal and distal members 60, 54 translated towards each other and the proximal and distal members 60, 54 detached from the proximal and distal hub members 58, 52. FIG. 6B illustrates the connector 102 snap fitting with the port 68 of the distal hub member 52 when the distal hub member 52 is connected with the proximal hub member 58.

Figure 7:
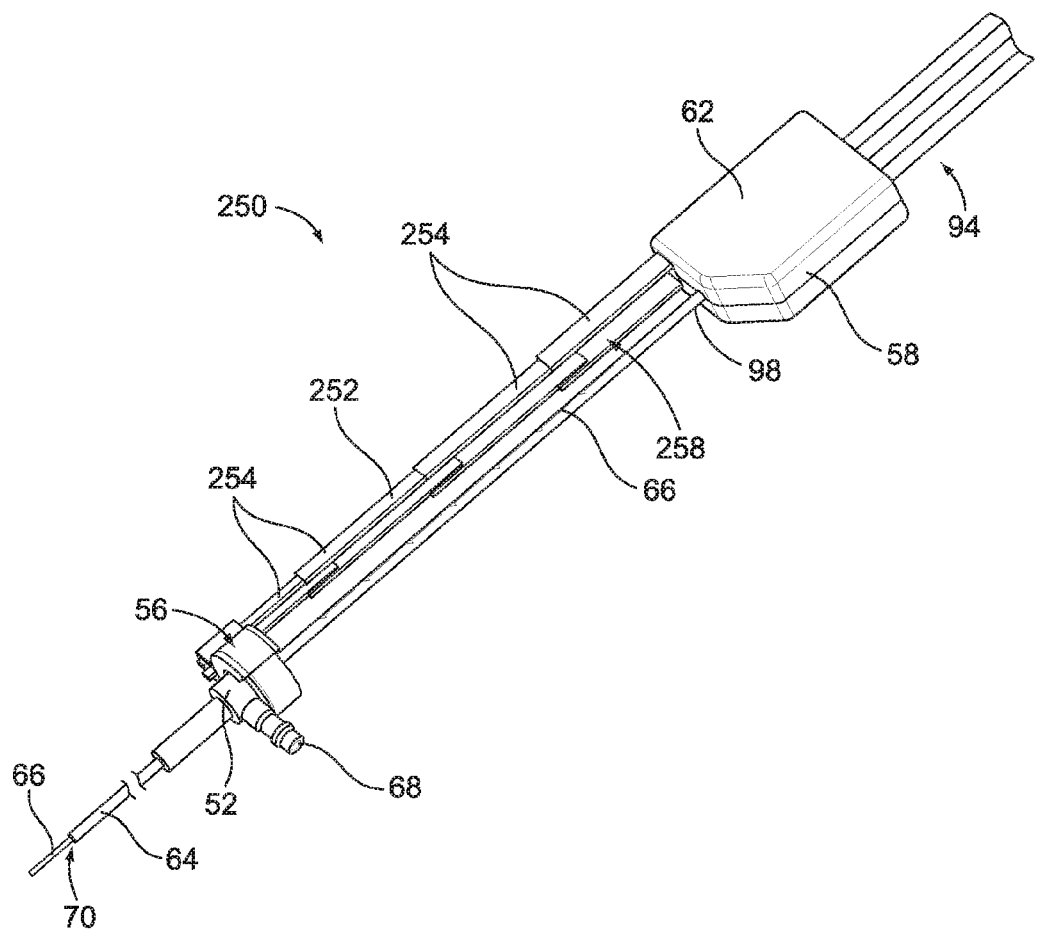
FIG. 7 is an isometric view of a further embodiment of a hub assembly in an extended state.
Figure 8:
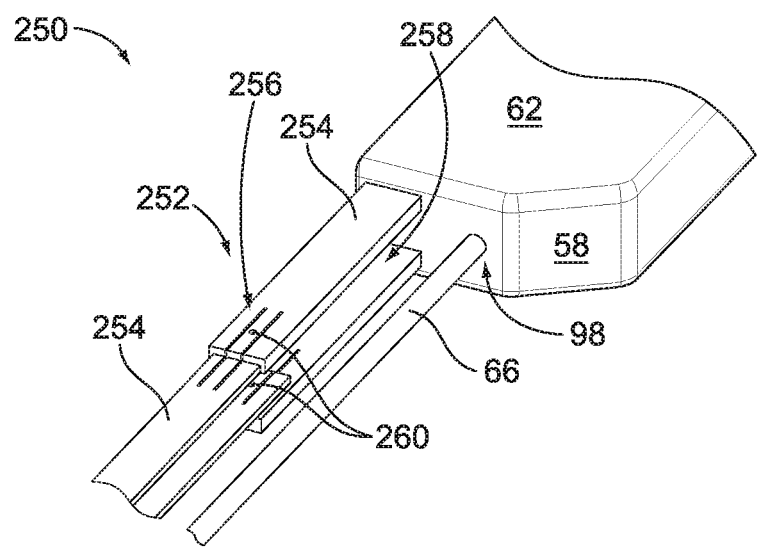
FIG. 8 is an isometric view of a close-up of a telescoping portion of FIG. 7.

A further embodiment of a hub assembly 250 is illustrated in FIGS. 7-9. This embodiment includes features that are similar to the embodiments described hereinabove with regard to FIGS. 1-6. However, in this embodiment, the proximal and distal assemblies 62, 56 include the proximal and distal hub members 58, 52, respectively, and are connected by a telescoping member 252. FIG. 7 illustrates the telescoping member 252 in an extended state; however, the telescoping member 252 allows the proximal and distal assemblies 62, 56 (and corresponding proximal and distal hub members 58, 52) to translate longitudinally relative to one another. A connection between the proximal hub member 58 and the distal hub member 52 may be established when the telescoping member 252 is in a longitudinally collapsed state. The telescoping member 252 is disposed laterally adjacent to the inner catheter 66, which exits the proximal hub member 58 at the second hub aperture 98. Alternatively, a plurality of telescoping members 252 may be provided to connect the proximal and distal hub members 58, 52, whereby two telescoping members 252 may be on opposite sides of the inner catheter 66, or two telescoping members 252 may be adjacent to one another.

As shown in FIGS. 7-9, the telescoping member 252 comprises a collapsible beam including multiple beam segments 254. The multiple beam segments 254 include a translation lock 256 to secure the telescoping member 252, and thereby secure the proximal and distal assemblies 62, 56 respectively including the proximal and distal hub members 58, 52 in a fixed state. The translation lock 256 may be integral to the design or a removable component. The telescoping member 252 may have any multiple number of beam segments 254 from as little as two to as many as 15 or 20, or as many that are desired or needed. For example, additional beam segments 254 may be added for a longer telescoping member 252. In this embodiment, each beam segment 254 comprises a channel 258 that nests inside or outside of an adjacent beam segment 254 such that all of the beam segments may be collapsed to the size of the largest of the beam segments 254. The beam segments may be rectangular, polygonal, circular, elliptical, pentagonal, hexagonal, and the like configurations such as to allow telescoping and translation along adjacent channels 258.

Figure 9A:
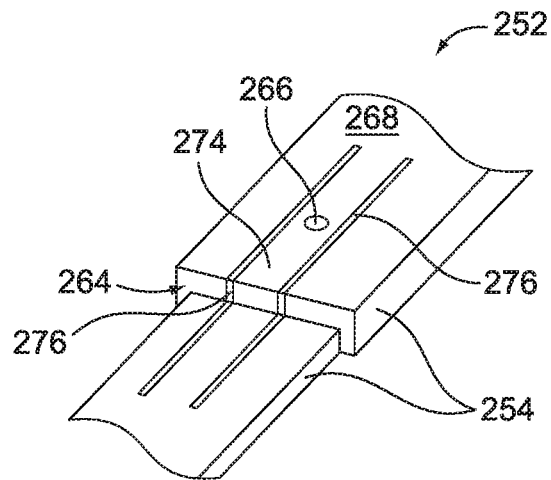
FIG. 9A is an isometric view of a close-up of a first telescoping portion of FIG. 8.
Figure 9B:
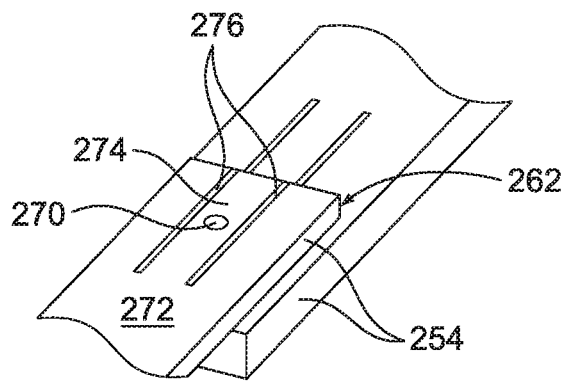
FIG. 9B is an isometric view of a close-up of a second telescoping portion of FIG. 8.

The translation lock 256 may secure the telescoping member 252 in a fixed collapsed state, a fixed fully extended state, or a fixed partially expanded state. Referring to FIGS. 8-9B, in this embodiment, the translation lock 256 comprises spherical detents 260 disposed proximate to proximal and/or distal ends 262, 264 of each beam segment 254. Referring to FIGS. 9A-9B, each spherical detent 260 is configured to include a bump (or extension) 266 on a first side 268 of each beam segment 254 and/or a divot (or depression) 270 on a second side 272 of each beam segment 254 such that when first and second adjacently nested beam segments 254 longitudinally coincide, the bump 266 of the first beam segment 254 is captured within the divot 270 of the second beam segment 254. The first and second beam segments 254 are thus secured from further translation without the application of sufficient force to disengage the bump 266 from the divot 270. Each of the spherical detents 260 may be disposed on a cantilevered arm 274 of the beam segment 254, wherein the cantilevered arm 274 is defined by slots 276 disposed through the beam segment 254, as illustrated in FIGS. 9A-9B.

In other embodiments, the translation lock 256 may include other structural elements as known in the art that secure the proximal and distal assemblies 62, 56 in a fixed longitudinal state. For example, the hub 50 as described hereinabove with regard to FIGS. 1-4 may utilize the set screw 78 disposed through the aperture 80 to fixedly secure one or both of the proximal and distal members 60, 54 in a fixed longitudinal state.

A further embodiment of a hub 350 that is similar to the hub 250 described with regard to FIGS. 7-9 hereinabove, is illustrated in FIGS. 10-12. In this embodiment, a telescoping member 352 includes a collapsible tube 354 disposed within beam segments 356 and adapted to accommodate the inner catheter 66 therethrough. In this embodiment, the telescoping member 352 is adapted to be disposed around the inner catheter 66 and covers the second hub aperture 98, as shown in FIG. 10A. The collapsible tube 354 is adapted to be disposed centrally through the proximal hub member 58 and the distal hub member 52. As such, the proximal and distal hub members 58, 52 may include a central lumen for coaxially accommodating the collapsible tube 354. A tube attachment member 362 is fixably attached to a proximal end of the collapsible tube 354, as shown in FIGS. 10-11. The tube attachment member 362 further comprises at least two tabs 364 that project distally from the proximal side of the tube attachment member 362. The tube attachment member 362 may attach to the proximal assembly 62 by the tabs 364 laterally flexing and snapping into slots 366, which in this embodiment are configured to receive tabs 364 at the proximal end of proximal assembly 62.

The hub assembly 350 is illustrated in an expanded state in FIGS. 10A-B and in a collapsed state in FIG. 11, which illustrates that the proximal hub member 58 connects to the distal hub member 52 when the telescoping member 352 is in a longitudinally collapsed state. At least two tabs 358 extend proximally from the distal assembly 56, which comprises the distal hub member 52. At least two slots 360 face distally from the proximal assembly 62, which comprises the proximal hub member 58. In the collapsed state illustrated in FIG. 11, the tabs 358 laterally flex and snap into the slots 360 to provide a translation lock 256 in the collapsed state. The plurality of first hub apertures 96, as described hereinabove with regard to FIGS. 1-4, may be disposed in any configuration and on any surface or surfaces of the proximal hub member 58 or the tube attachment member 362. For example, the plurality of first hub apertures 96 are disposed on a proximal surface of the proximal hub member 58, as illustrated in FIG. 12.

Figure 13:
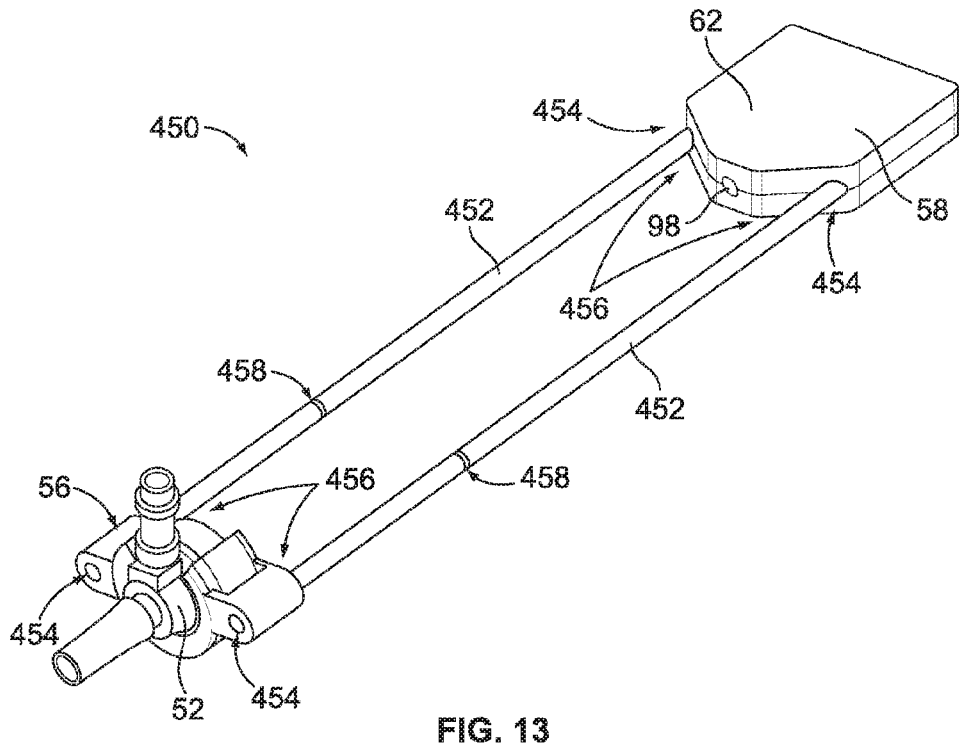
FIG. 13 is an isometric view of still another embodiment of a hub assembly in an extended state.
Figure 14:
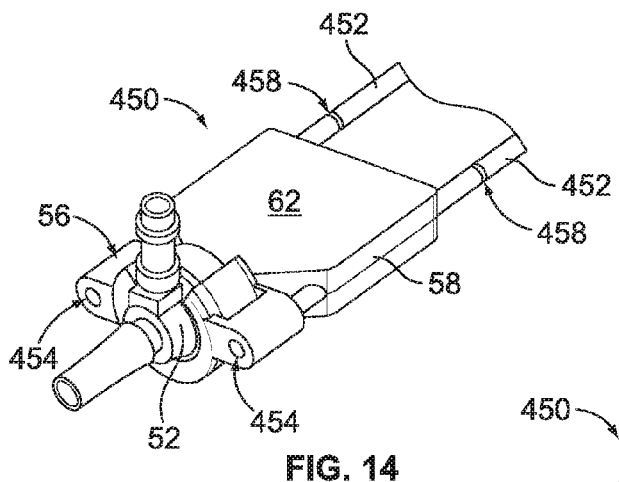
FIG. 14 is an isometric view of the hub assembly of FIG. 13 in a collapsed state.
Figure 15:
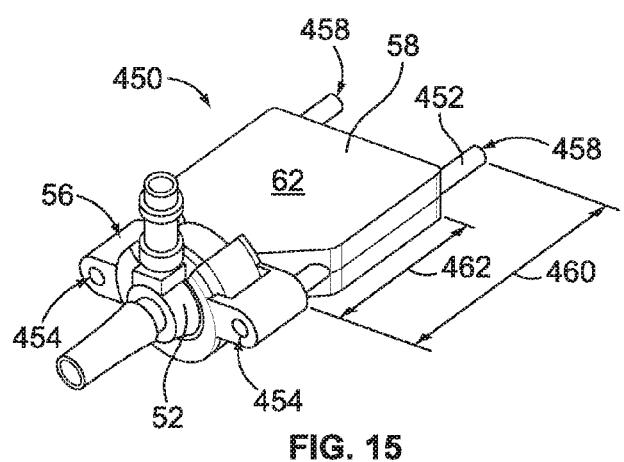
FIG. 15 is an isometric view of the hub assembly of FIG. 13 in a connected and broken-away state.

Another embodiment of a hub assembly 450 is illustrated in FIGS. 13-15. The hub assembly 450 shares many common features with the hubs 50, 150, 250, 350 described hereinabove with regard to FIGS. 1-12. However, in this embodiment, the distal assembly 56 including the distal hub 52, or the proximal assembly 62 including the proximal hub member 58 may be attached to a breakaway elongate member 452 by a fixed attachment. The fixed attachment may be via a fastener, an adhesive, a press fit, a snap fit, or via any method of attachment. At least two breakaway elongate members 452 may be utilized as illustrated in FIGS. 13-15; however a single breakaway elongate member 452 or three or more breakaway elongate members 452 may be utilized as desired or as needed. The use of two or more breakaway elongate members 452 may provide enhanced resistance to relative and absolute rotation of the proximal and distal assemblies 62, 56.

Further, one or both of the proximal and distal assemblies 62, 56 may be slidably attached to the breakaway elongate member 452 via an aperture 454 disposed longitudinally through the proximal assembly 62 and/or the distal assembly 56. The aperture 454 is adapted to coaxially accommodate the breakaway elongate member 452 and is further adapted to allow the proximal assembly 62 and/or the distal assembly 56 to slide longitudinally on the breakaway elongate member 452. A slidable connection between the breakaway elongate member 452 and one or both of the proximal assembly 62 and the distal assembly 56 may be facilitated as described hereinabove for the hub 50.

The hub 450 is illustrated in an extended state in FIG. 13 and may be secured in the extended state by a translation lock 456 comprising, for example, a press fit between the breakaway elongate member 452 and one or both of the proximal and distal assemblies 62, 56. Alternatively, the translation lock 456 may be an aperture through the proximal and distal assemblies and set screw disposed therethrough to lock the elongate member in a surface groove as described previously. In FIG. 14, the proximal and distal assemblies 62, 56 have been brought together to a collapsed state via relative longitudinal translation along the breakaway elongate member 452. The hub 450 may be secured in the collapsed state by a translation lock 456 comprising, for example, a press fit between the breakaway elongate member 452 and one or both of the proximal and distal assemblies 62, 56. Further, in the collapsed state illustrated in FIG. 14, the proximal and distal assemblies 62, 56 and the proximal and distal hub members 58, 52 respectively included therein are in contact with one another and may be connected to one another. Such connection may be via a quick-connect fitting, a press fit, a snap fit, a threaded connection, or by any method of detachable attachment as known in the art.

Subsequent to connection of the proximal and distal assemblies 62, 56 in the collapsed state, the breakaway elongate member 452 may be left on the hub 450, as illustrated in FIG. 14. However, the breakaway elongate member 452 may alternatively be broken away as illustrated in FIG. 15 to provide a shorter hub 450 and eliminate portions of the breakaway elongate member 452 that may snag on other apparatus or clothing. Accordingly, each breakaway elongate element 452 includes a region of weakness 458 to facilitate breakage by application of a transverse force or torsional shear force thereto.

The region of weakness 458 may comprise a region of the breakaway elongate member 452 that is relatively thinner than the portion of the breakaway elongate member 452 outside of the region. The region of weakness 458 is disposed on the breakaway elongate member 452 a distance from one of the proximal and distal hub members 58, 52 that is fixedly attached thereto, wherein the distance is about equal to or greater than the longitudinal dimension of the other of the proximal and distal hub members. For example, referring to FIG. 15, the distance between the region of weakness 458 and a proximal side of the distal hub member 52 is identified by reference numeral 460. Likewise, the longitudinal dimension of the proximal hub member 58 is identified by reference numeral 462. As long as the distance 460 is about equal to or greater than the distance 462, the region of weakness 458 will be near or proximal to the proximal surface of the proximal hub member 58, thereby facilitating breakage at the region of weakness 458.

Figure 16:
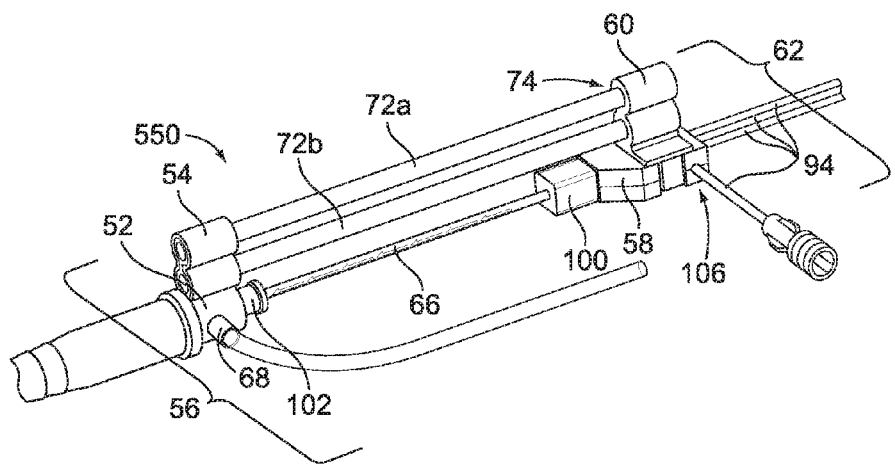
FIG. 16 is an isometric view of a further embodiment of a hub assembly in an extended state.

A further embodiment of a hub 550 illustrated in FIG. 16 is similar to the hubs 50, 150, 250, 350, 450 described hereinabove with regard to FIGS. 1-15. However, in this embodiment the elongate member 72 includes a plurality of elongate members, for example, 72A and 72B, as illustrated. In this embodiment, both of the elongate members 72A, 72B are disposed on the same side of the inner catheter 66. In other embodiments, one of the elongate members 72A, 72B is disposed on each side of the inner catheter 66. Further embodiments include three or more elongate members 72 arranged on one or both sides of the inner catheter 66 for additional stability of longitudinal movement of the proximal and distal assemblies 62, 56.

The elongate members 72A, 72B are attached, for example, to the proximal member 60 via a press fit into at least two apertures 74. Alternatively, the elongate members 72A, 72B are integrally fabricated with the proximal assembly 62 or the distal assembly 56. The distal assembly 56 or the proximal assembly 62 slidably attaches to the elongate members 72A, 72B. A translation lock 256 is provided to fixedly secure distal assembly 56 in a fixed longitudinal state relative to the proximal assembly 62. In one embodiment, the translation lock 256 may be a press fit between the distal assembly 56 and one or both of the elongate members 72A, 72B, or an aperture through the distal assembly and set screw therethrough to engage a surface groove on the elongate members as described previously. In this embodiment, the proximal and distal members 60, 54 are integrally fabricated with or permanently attached to the proximal and distal hub members 58, 52, respectively. In another embodiment, the proximal and distal members 60, 54 are detachably attached to the proximal and distal hub members 58, 52, respectively. The proximal and distal member 60, 54 longitudinally align apertures 74 such that elongate member 72A, 72B may fit therewith.

In the embodiment for the hub 550, three of the plurality of first hub apertures 96 (not shown) are disposed on a proximal surface of the proximal hub member 58 to accommodate the plurality of tubes 94, and a fourth first hub aperture 106 is disposed on a lateral surface of the proximal hub member 58 to accommodate the tube 94. The proximal hub member 58 connects to the distal hub member 52 via connection of the first and second connectors 100, 102. The method of connection may be, for example, a quick-connect fitting, a press fit, a snap fit, a threaded connection, a magnetic connection, or any method of detachable attachment.

Figure 17:
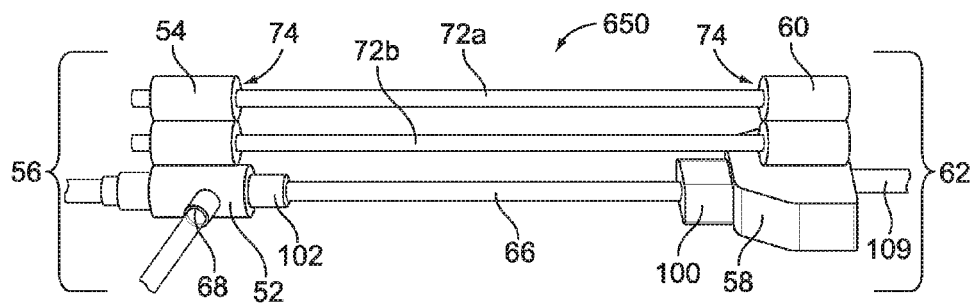
FIG. 17 is an isometric view of another embodiment of a hub assembly in an extended state.
Figure 18:
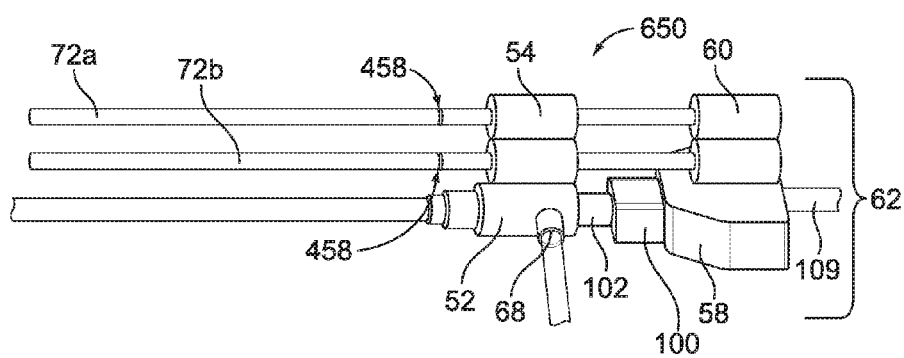
FIG. 18 is an isometric view of the hub assembly of FIG. 17 in a connected state.
Figure 19A:
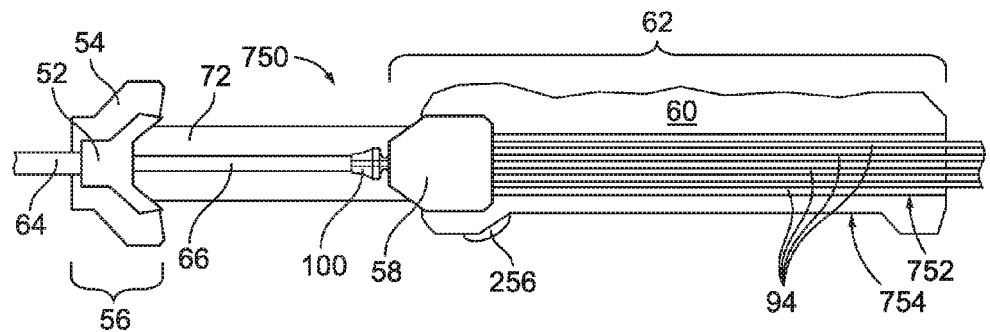
FIG. 19A is a plan view of yet another embodiment of a hub assembly in an extended state.
Figure 19B:
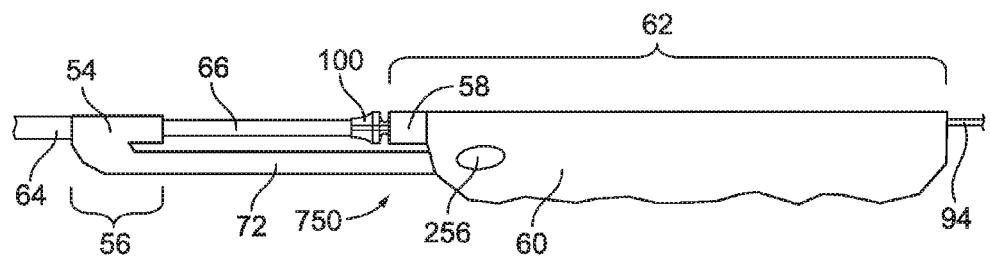
FIG. 19B is a side view of the hub assembly of FIG. 19A in an extended state.

FIGS. 17-18 illustrate another embodiment of a hub 650 that is very similar to the hub 550 described in regard to FIG. 16. The distal assembly 56 and distal member 54 is longitudinally translated along the elongate members 72A, 75B, whereby the apertures 74 of the distal member coaxially engage the elongate members 72B, 72A. However, the hub 650 includes a single inlet tube 109 that comprises the plurality of tubes 94. In another embodiment, the elongate members 72A, 72B each include a region of weakness 458, as described hereinabove with regard to FIGS. 13-15, to facilitate breakage by application of a transverse force or torsional shear force thereto. Referring to FIG. 18, for example, in this embodiment, the region of weakness 458 is disposed on each elongate member 72A, 72B just distal to the distal hub member 52 when the hub 550, 650 is in a connected state via connectors 102, 100. Such placement of the regions of weakness 458 facilitates removal of portions of the elongate members 72A, 72B that may snag on other apparatus or clothing when the hub 550, 650 is in a connected state.

A further embodiment of a hub 750 illustrated in FIGS. 19A-20B is similar to the hubs 50, 150, 250, 350, 450, 550, and 650 described hereinabove with regard to FIGS. 1-18. However, in this embodiment, the proximal member 60 is shaped to be held in a user's hand and includes a first side (See FIG. 19A) designed to detachably accommodate the proximal hub member 58 via, for example, a snap fit; however, detachable attachment of the proximal hub member 58 to the proximal member 60 may be via a fastener, a quick-connect fitting, an adhesive, a press fit, a clamp, a snap fit, a threaded connection, or by any method of detachable attachment as known in the art. The proximal member 60 also includes a plurality of channels 752 disposed within the proximal member 60 to accommodate the plurality of tubes 94.

In this embodiment, the elongate member 72 is integrally fabricated with the distal member 54 and slides into the proximal member 60. The distal member 54 detachably accommodates the distal hub member 52 via, for example, a snap fit; however, detachable attachment of the distal hub member 52 to the distal member 54 may be via a fastener, a quick-connect fitting, an adhesive, a press fit, a clamp, a snap fit, a magnetic connection, a threaded connection, or by any method of detachable attachment.

A second side of the proximal member 60 includes a recess 754 (See FIGS. 19A-20B) and a translation lock 256 disposed at a distal end of the recess 754. The translation lock 256 engages the elongate member 72 through the proximal member 60 to secure the proximal and distal assemblies 62, 56 a fixed distance apart and thereby lock out relative motion between the proximal member 60 (and the proximal hub 58) and the distal member 54 (and the distal hub 52) until such time as the medical professional desires relative motion between the proximal and distal hubs 58, 52. Engagement between the translation lock 256 and the elongate member 72 may be, for example, via a press fit, an internal ratchet arrangement, longitudinally spaced detents, screw and groove, or other any other engagement. The translation lock on the elongate member 72 controls the linear motion of the elongate member 72, which may be an outer sheath, which prevents a distal filter or stent from prematurely being deployed due to friction or resistance during insertion of the outer sheath into the body or subject.

Figure 20A:
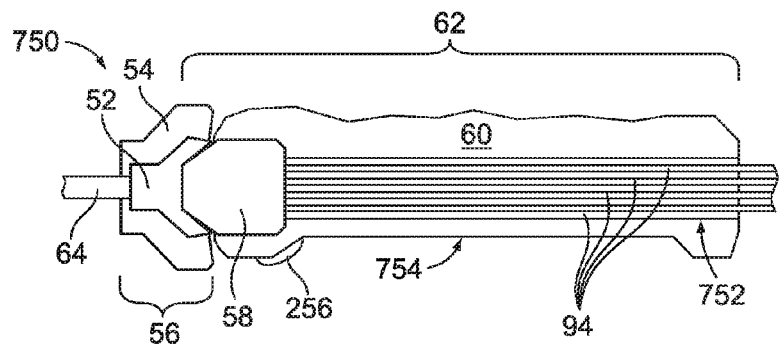
FIG. 20A is a plan view the hub assembly of FIG. 19A in a connected state.
Figure 20B:
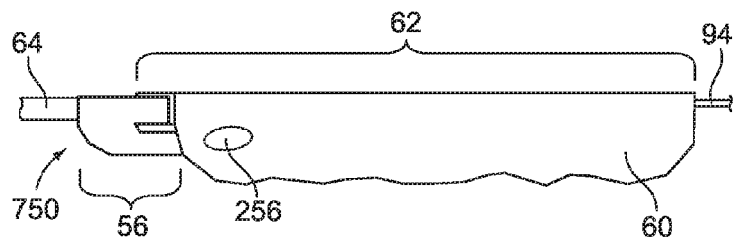
FIG. 20B is a side view of the hub assembly of FIG. 19A in a connected state.
Figure 21A:
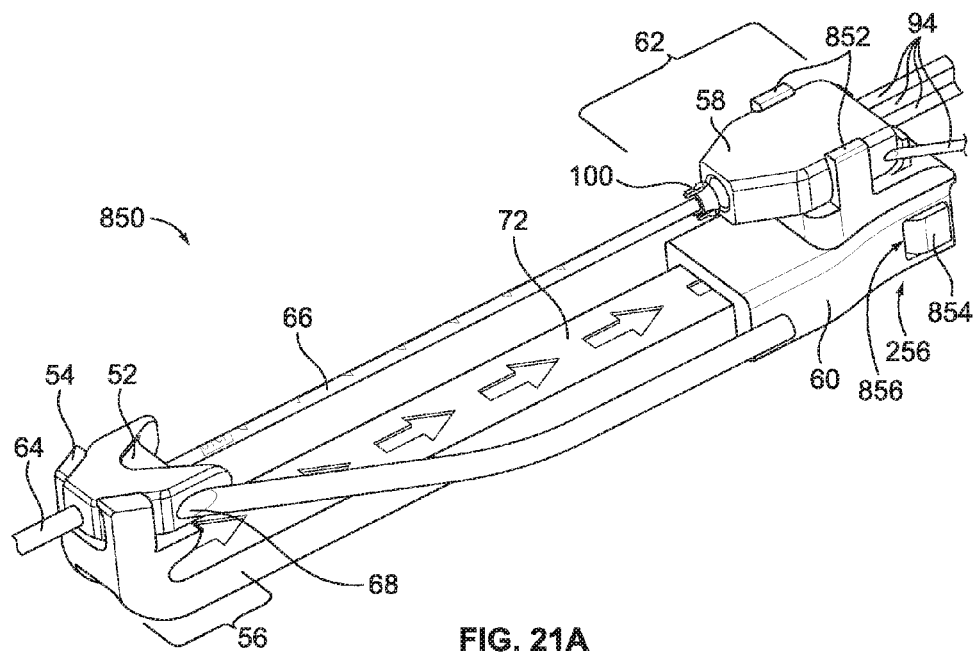
FIG. 21A is an isometric view of yet another embodiment of a hub assembly in an extended state.
Figure 21B:
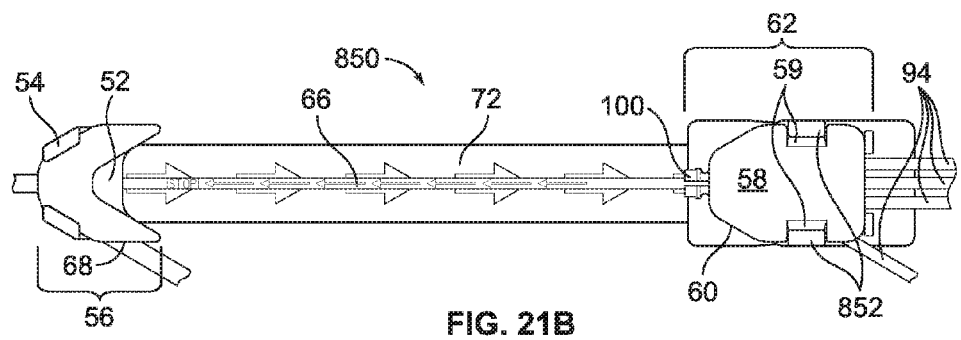
FIG. 21B is a plan view of the hub assembly of FIG. 21A in an extended state.
Figure 21C:
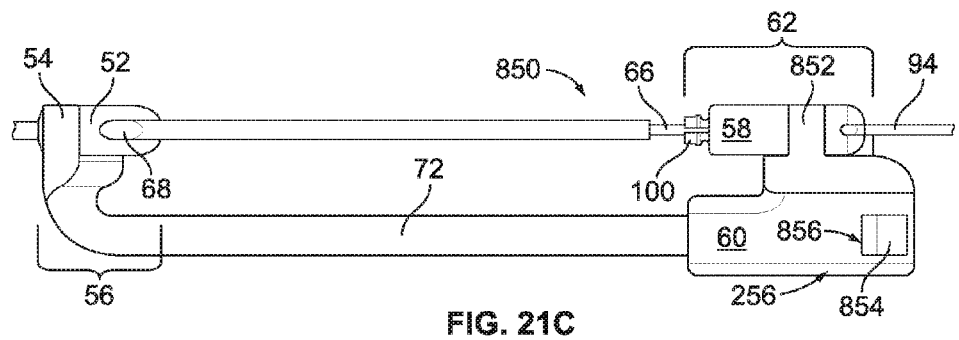
FIG. 21C is a side view of the hub assembly of FIG. 21A in an extended state.

Referring to FIGS. 20A and 20B, the proximal hub member 58 connects to the distal hub member 52 by any suitable means of detachable connection as is known in the art, including by way of example and not limitation, a quick-connect fitting, a press fit, a snap fit, magnetic connection, or a threaded connection. For example, referring to FIGS. 19B and 20B, in one embodiment the first connector 100 comprises a flexible snap fit member that snaps together with a complimentary snap fit member (not shown) disposed within the distal hub 52. The connector 100 on the proximal hub member 58 may snap fit within the lumen of the distal hub member 52. Alternatively, the proximal hub member 58 may include a trapezoidal or polygonal interface that mates with and is complimentary to a trapezoidal or polygonal interface on the distal hub member 52. The distal hub member 52 may radially deform onto the outer surface of the proximal hub member 58 to provide for further mechanical interlocking.

FIGS. 21A-22C illustrate another embodiment of a hub 850 that is similar to the hub 750 described hereinabove in regard to FIGS. 19A-20B except for the following differences. The hub 850 includes a proximal member 60 that is relatively smaller than the proximal member 60 of the hub 750. Further, the proximal member 60 in this embodiment includes a pair of arms 852 that are adapted to snap over the proximal hub member 58, which may include notches (not shown) and/or recesses 59 to accommodate the arms 852.

Figure 22A:
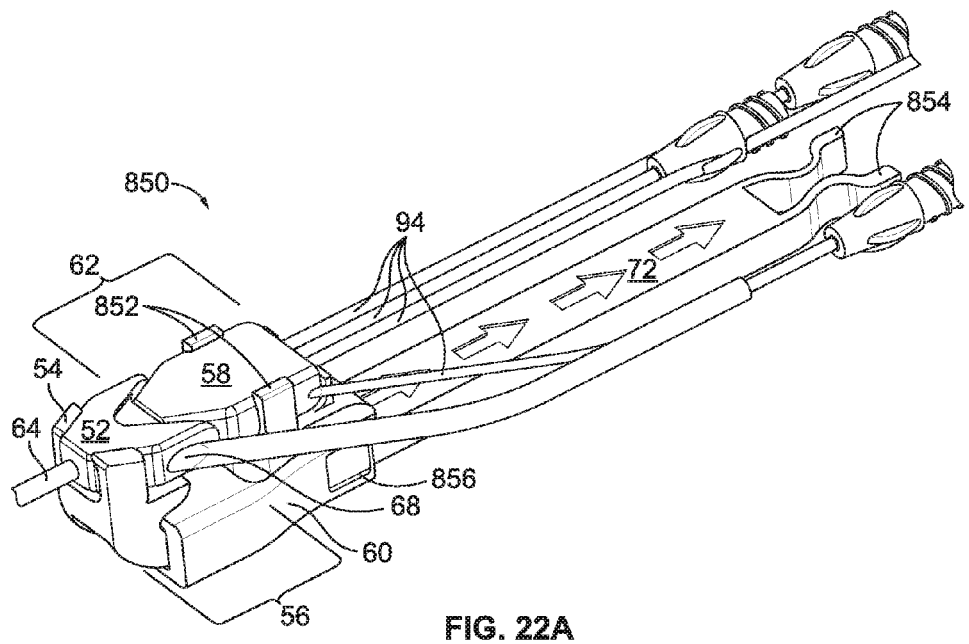
FIG. 22A is an isometric view of the hub assembly of FIG. 21A in a connected state.
Figure 22B:
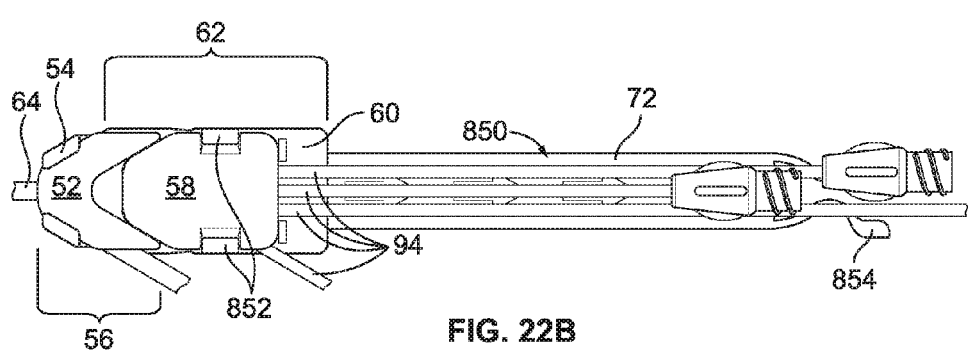
FIG. 22B is a plan view of the hub assembly of FIG. 21A in a connected state.
Figure 22C:
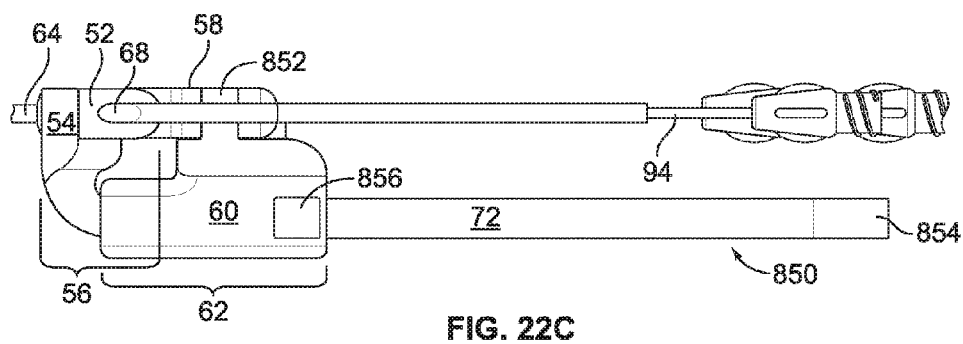
FIG. 22C is a side view of the hub assembly of FIG. 21A in a connected state.

In addition, in this embodiment, the translation lock 256 includes a pair of tabs 854 that are sufficiently outwardly biased so as to snap through apertures 856 when so aligned. Thus, relative motion between the proximal member 60 (and the proximal hub 58) and the distal member 54 (and the distal hub 52) may be locked out in the extended state, as illustrated in FIGS. 22A-22C. The translation lock 256 may be defeated by forcing the tabs 854 inwardly until the tabs 854 become disengaged from the apertures 856, thus allowing the proximal member 60 to slide distally relative to the elongate member 72. The tabs 854 can be connected together in a manner that prevents the extension lines of the catheter from being caught between the tabs 854, where the relative motion of the tabs 854 serving as a lock would not be compromised.

A hub assembly for a catheter is presented. The hub assembly provides kinking resistance to an inner catheter of a central access catheter during retraction of an outer catheter of the central access catheter. Features such as a removable assembly, breakaway members, and a telescoping member facilitate compactness and ease of use for a medical professional.

It will be appreciated by those skilled in the art that changes could be made to the embodiments described hereinabove without departing from the broad concepts disclosed therein. Various modifications, equivalent processes, as well as numerous structures to which the present disclosure may be applicable will be readily apparent to those of skill in the art to which the present disclosure is directed upon review of the present specification. It is understood, therefore, that this disclosure is not limited to the particular embodiments disclosed, but it is intended to cover modifications that may include a combination of features illustrated in one or more embodiments with features illustrated in any other embodiments. Accordingly, this description is to be construed as illustrative only and is presented for the purpose of enabling those skilled in the art to make and use the hubs described herein and to teach the best mode of carrying out the same.

We claim:

1. A catheter hub and handle assembly, comprising:
   a distal hub member coupled to a flexible outer catheter member adapted for intravascular delivery of fluids and a proximal hub member coupled to a flexible inner catheter member adapted for intravascular delivery of fluids, the flexible inner catheter member being disposed within the flexible outer catheter member;
   a distal handle member adapted to detachably couple to the distal hub member;
   a proximal handle member adapted to detachably couple to the proximal hub member and having a receiving recess in a distal section of the proximal handle member, the proximal handle member further comprised of a plurality of unenclosed channels formed on a surface of the proximal handle member adapted to accommodate a plurality of tubes;
   the plurality of tubes configured to be in fluid communication with the flexible inner catheter; and
   an elongate handle member proximally extending from the distal handle member and passing into the receiving recess and movably coupled to the proximal handle member such that the distal handle member is capable of longitudinal translation relative to and independent of the proximal handle member along a longitudinal axis of the elongate member.

2. The catheter hub of claim 1 wherein the proximal handle member is adapted to detachably accommodate the proximal hub via any of the following: a fastener, a quick-connect fitting, an adhesive, a press fit, a clamp, a snap fit, a magnetic connection, or a threaded connection.

3. The catheter hub of claim 1 wherein the distal handle member is adapted to detachably accommodate the distal hub via any of the following: a fastener, a quick-connect fitting, an adhesive, a press fit, a clamp, a snap fit, a magnetic connection, or a threaded connection.

4. The catheter hub of claim 1 wherein the elongate handle member is integrally fabricated with the distal handle member and is adapted to slide into the proximal handle member.

5. The catheter hub of claim 1 wherein the proximal handle member further comprises a recess and a translation lock disposed at a distal end of the recess.

6. The catheter hub of claim 5 wherein the proximal handle member further comprises a receiving opening which is configured to receive the elongate handle member there through.

7. The catheter hub of claim 6 wherein the translation lock engages the elongate handle member through the proximal handle member to secure the proximal handle member to the distal handle member and fix relative motion between the proximal handle member and distal handle member.

8. The catheter hub of claim 7 wherein the engagement between the translation lock and the elongate handle member may be through any of the following: a press fit, a snap fit, an internal ratchet arrangement, longitudinally spaced detents, or a screw and groove.

9. The catheter hub of claim 1 wherein the proximal hub member is detachably connected to the distal hub member.

10. The catheter hub of claim 9 wherein the proximal hub member is detachably connected to the distal hub member via any one of the following: a quick-connect fitting, a press fit, a snap fit, magnetic connection, or a threaded connection.

11. The catheter hub of claim 10 wherein the proximal hub member comprises a first connector including a flexible snap fit member configured to snap together with a complimentary second connector disposed on the distal hub member.

12. The catheter hub of claim 11 wherein the second connector is a lumen of the distal hub member.

13. The catheter hub of claim 11 wherein the first connector is a polygonal interface and the second connector is a complimentary polygonal interface.

14. The catheter hub of claim 9 wherein the distal hub member is configured to radially deform onto an outer surface of the proximal hub member to provide further mechanical interlocking.

15. The catheter hub of claim 1, wherein the proximal handle member is configured to be gripped by a user thereof.

16. The catheter hub of claim 1 wherein the distal handle member comprises lateral projections adapted to accommodate a finger on a distal side of each of the lateral projections.

* * * * *